(12) United States Patent
Mueller et al.

(10) Patent No.: US 10,544,169 B2
(45) Date of Patent: Jan. 28, 2020

(54) PROCESS FOR ORGANOCHLOROSILANE PRODUCTION IN THE FLUIDIZED BED PROCESS

(71) Applicant: Wacker Chemie AG, Munich (DE)

(72) Inventors: Michael Mueller, Burghausen (DE); Natalia Sofina, Burghausen (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 16/093,708

(22) PCT Filed: May 12, 2016

(86) PCT No.: PCT/EP2016/060701
§ 371 (c)(1),
(2) Date: Oct. 15, 2018

(87) PCT Pub. No.: WO2017/178080
PCT Pub. Date: Oct. 19, 2017

(65) Prior Publication Data
US 2019/0127398 A1   May 2, 2019

(30) Foreign Application Priority Data
Apr. 15, 2016 (DE) .................. 10 2016 206 414

(51) Int. Cl.
*C07F 7/16* (2006.01)
*B01J 8/18* (2006.01)
*B01J 23/72* (2006.01)

(52) U.S. Cl.
CPC ..... *C07F 7/16* (2013.01); *B01J 8/18* (2013.01); *B01J 23/72* (2013.01)

(58) Field of Classification Search
None
See application file for complete search history.

(56) References Cited

U.S. PATENT DOCUMENTS

| 4,176,710 A | 12/1979 | Gansauge |
| 5,981,784 A | 11/1999 | Kalchauer |

(Continued)

FOREIGN PATENT DOCUMENTS

| DE | 2704975 A1 | 8/1978 |
| DE | 19817775 A1 | 10/1999 |

(Continued)

OTHER PUBLICATIONS

Kuz'min N G Et Al: Study of Heat Transfer in a Fluidized Bed of Silicon-copper Alloy in a Model of an Industrial Reactor for the Synthesis of Organochlorosilanes Soviet Chemical Industry, McElroy, Austin, TX, US, vol. 14, No. 5, Jan. 1, 1982 (Jan. 1, 1982), pp. 595-601, XP008182487, ISSN: 0038-5344.

(Continued)

*Primary Examiner* — Clinton A Brooks
(74) *Attorney, Agent, or Firm* — Brooks Kushman P.C.

(57) ABSTRACT

A process for producing organochlorosilanes in a fluidized bed reaction comprises reacting haloorganic reaction gas with a catalytic composition comprising silicon, copper catalysts and promoters, in a fluidized bed reactor, wherein the hydraulic diameter of the fluidized bed reactor dhyd,
the superficial gas velocity in the fluidized bed reactor uL and
the particle Sauter diameter of the catalytic composition d32 are selected such that,
in a Cartesian coordination system in which Ar is plotted against Re, points on the surface are formed wherein the surface is limited by equations 1 and 2

$Ar = 2 \cdot 10^{-5} \cdot Re^2 + 0.08 * Re - 120$   Equation 1:

$Ar = 2 \cdot 10^{-5} \cdot Re^2 - 1.07 * Re + 14100$   Equation 2:

wherein the lower limit Ar=0.5 and (Continued)

the upper limit Ar=3000. The invention also relates to a method for selecting reaction parameters for producing organochlorosilanes.

7 Claims, 3 Drawing Sheets

(56) References Cited

U.S. PATENT DOCUMENTS

2001/0020108 A1  9/2001  Aramata
2014/0369771 A1  12/2014 Mautner

FOREIGN PATENT DOCUMENTS

DE  10053346 A1  5/2002
EP   2813285 A2  12/2014

OTHER PUBLICATIONS

Pan Zhang Et Al: Effect of Bed Characters on the Direct Synthesis of Dimethyldichlorosilane in Fluidized Bed Reactor Scientific Reports, vol. 5, Mar. 6, 2015 (Mar. 6, 2015), pp. 8827, XP055324940, DOI: 10.1038/srep08827.

PROCESS FOR ORGANOCHLOROSILANE PRODUCTION IN THE FLUIDIZED BED PROCESS

CROSS REFERENCE TO RELATED APPLICATIONS

This application is the U.S. National Phase of PCT Appln. No. PCT/EP2016/060701 filed May 12, 2016, which claims priority to German Application No. 10 2016 206 414.2 filed Apr. 15, 2016, the disclosures of which are incorporated in their entirety by reference herein.

BACKGROUND OF THE INVENTION

1. Field of the Invention

The invention relates to a process for producing organochlorosilanes in a fluidized bed reaction by reacting reaction gas comprising chloromethane with a catalytic composition, wherein the hydraulic diameter of the fluidized bed reactor $d_{hyd}$, the superficial gas velocity in the fluidized bed reactor $u_L$ and the particle Sauter diameter of the catalytic composition $d_{32}$ are specifically selected.

2. Description of the Related Art

In the Müller-Rochow direct synthesis, an organic compound having chlorine bound to carbon is reacted with silicon in the presence of copper catalysts and suitable promoters to give organochlorosilanes, particularly methylchlorosilanes (MCS). The highest possible productivity (amount of silanes formed per unit time and reaction volume); the highest possible selectivity—based on the most important target product $(CH_3)_2SiCl_2$; and also the highest possible silicon use) is demanded. The organochlorosilanes are produced industrially by a fluidized bed reaction. The MCS fluidized bed reaction is a very complex process, in which very many different influencing factors and areas of expertise converge. In the context of the MCS synthesis, DE2704975A describes heat exchange internals with the purpose of dissipating the heat of reaction of the exothermic reaction in order to achieve thereby a constant reaction temperature.

SUMMARY OF THE INVENTION

The invention relates to a process for producing organochlorosilanes in a fluidized bed reaction by reacting reaction gas, comprising an organic compound having chlorine bound to carbon, with catalytic composition comprising silicon, copper catalysts and promoters, in which very specific reaction parameters are employed.

DETAILED DESCRIPTION OF THE PREFERRED EMBODIMENTS

The fluidized bed reaction is thus carried out in a fluidized bed reactor, wherein the hydraulic diameter of the fluidized bed reactor $d_{hyd}$, the superficial gas velocity in the fluidized bed reactor $u_L$ and
the particle Sauter diameter of the catalytic composition $d_{32}$
are selected such that,
in a Cartesian coordination system, in which Ar is plotted against Re, points on the surface are formed wherein the surface is limited by equations 1 and 2

$$Ar = 2 \cdot 10^{-5} \cdot Re^2 + 0.08 * Re - 120 \qquad \text{Equation 1:}$$

$$Ar = 2 \cdot 10^{-5} \cdot Re^2 - 1.07 * Re + 14100 \qquad \text{Equation 2:}$$

wherein the lower limit Ar=0.5 and
the upper limit Ar=3000,
where Ar is the dimensionless Archimedes number, which is determined by equation 3

$$Ar = g \cdot \frac{d_{32}^3}{v_{F2}} \cdot \frac{\rho_P - \rho_F}{\rho_F} \qquad \text{Equation 3}$$

where
g is the acceleration due to gravity [m/s²],
$d_{32}$ is the particle Sauter diameter [m],
$\rho_P$ is the particle solid density [kg/m³],
$\rho_F$ is the fluid density [kg/m³],
$v_F$ is the kinematic viscosity of the fluid [m²/s],
where Re is the dimensionless Reynolds number, which is determined by equation 4

$$Re = \frac{u_L \cdot d_{hyd}}{v_{Fluid}} \qquad \text{Equation 4}$$

where
$u_L$ is the superficial gas velocity in the fluidized bed reactor [m/s],
$d_{hyd}$ is the hydraulic plant diameter [m] in the fluidized bed reactor, which is determined by equation 5

$$d_{hyd} = \frac{4 * A_{q,free}}{U_{ges,wet}} \qquad \text{Equation 5}$$

where
$A_{q,free}$ is the free cross-sectional flow [m²] in the fluidized bed reactor and
$U_{ges,wet}$ corresponds to the wet circumference [m] in each case of all internals in the fluidized bed reactor.

The invention produces a correlation between constructive features (internals), the particle sizes of the constituents of the catalytic composition used and the operating conditions in the fluidized bed reactor, whereby optimal ranges for the organochlorine synthesis can be determined. This makes it possible to optimize fluidized bed reactions for producing organochlorosilanes.

Figure 2:
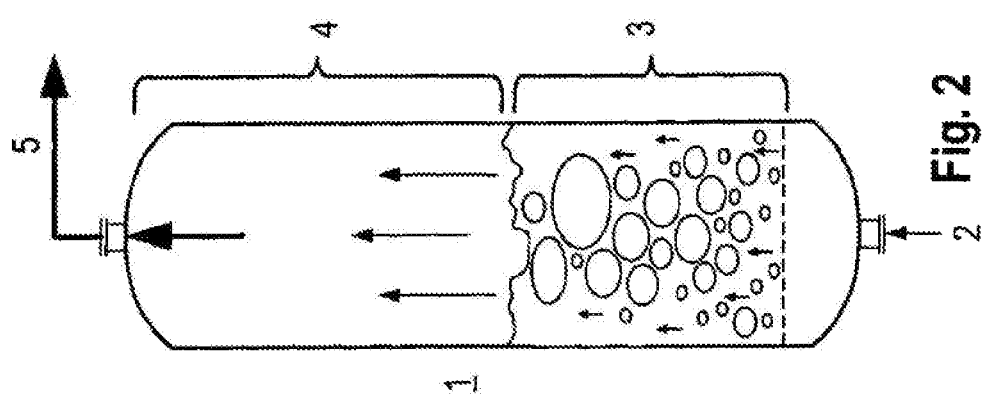
FIG. 2 illustrates a fluidized bed reactor.

The fluidized bed reactor (1) is illustrated in FIG. 2. The reaction gas (2) is preferably blown into the catalytic composition from below, whereby the particles of the catalytic composition are fluidized and the chemical reaction for producing organochlorosilanes takes place between the catalytic composition and the gas phase in the range of the fluidized bed (3). A portion of the particles is transported with the gas stream from the fluidized bed (3) into the freeboard (4). The freeboard (4) is characterized by a very low solid density, wherein this decreases in the direction of the reactor outlet. The proportion of particles which exits the reactor with the gas stream is referred to as the particle discharge (5).

In detailed investigations of the fluid dynamics in fluidized bed reactors with heat exchange internals, it has been found that these internals, depending on constructive features, also have an influence on the fluid dynamics of the fluidized bed and therefore on the productivity of the fluidized bed reactor.

The correlations discovered in this case impact firstly the residence time (1) of the reactive organic compound having chlorine bound to carbon, in particular chloromethane, in the fluidized bed reactor, and secondly on the discharge of silicon particles (2) from the fluidized bed reactor:

(1) The higher the residence time and the more homogeneous the distribution of the reaction gas in the fluidized bed reactor, the more organic compound having chlorine bound to carbon is converted, i.e. the more productive the fluidized bed reactor. With increasing internals surface, the ascending gas bubbles are slowed down and therefore the gas residence time increases.

(2) The Si particle discharge from the fluidized bed reactor, which occurs by "entrainment" of the silicon particles with the gas stream, depends on the particle size, the fill level in the fluidized bed reactor, on the amount of reaction gas (gas flow rate) continuously fed, the system pressure and also on the reactor internals.

The productivity of the fluidized bed reactor increases in principle with increasing fill level of catalytic composition, with increasing gas flow rate and with the use of smaller particle sizes of the catalytic composition (greater reaction surface). In addition to the influence of the internals on the gas residence time in the fluidized bed reactor, there is also a correlation between sheet-like internals and the discharge of silicon particles. The discharge here is influenced by two mechanisms. Firstly, the gas bubbles are slowed down with increasing internals surface area so that fewer silicon particles are ejected at the fluidized bed surface. Secondly, coarser silicon particles especially are slowed down in the freeboard by more internals surface area and are therefore retained in the fluidized bed. By means of specific modifications of internals, the productivity of the fluidized bed reactor can then be increased by increasing the gas flow rate and/or the fill level of catalytic composition or by decreasing the particle size of the catalytic composition particles. The relationship of these quantities, which are linked to one another and which influence one another, may be understood by means of dimensionless parameters. On this basis, working ranges are defined in which organochlorosilanes may be produced effectively and economically in fluidized bed reactors.

Figure 1:
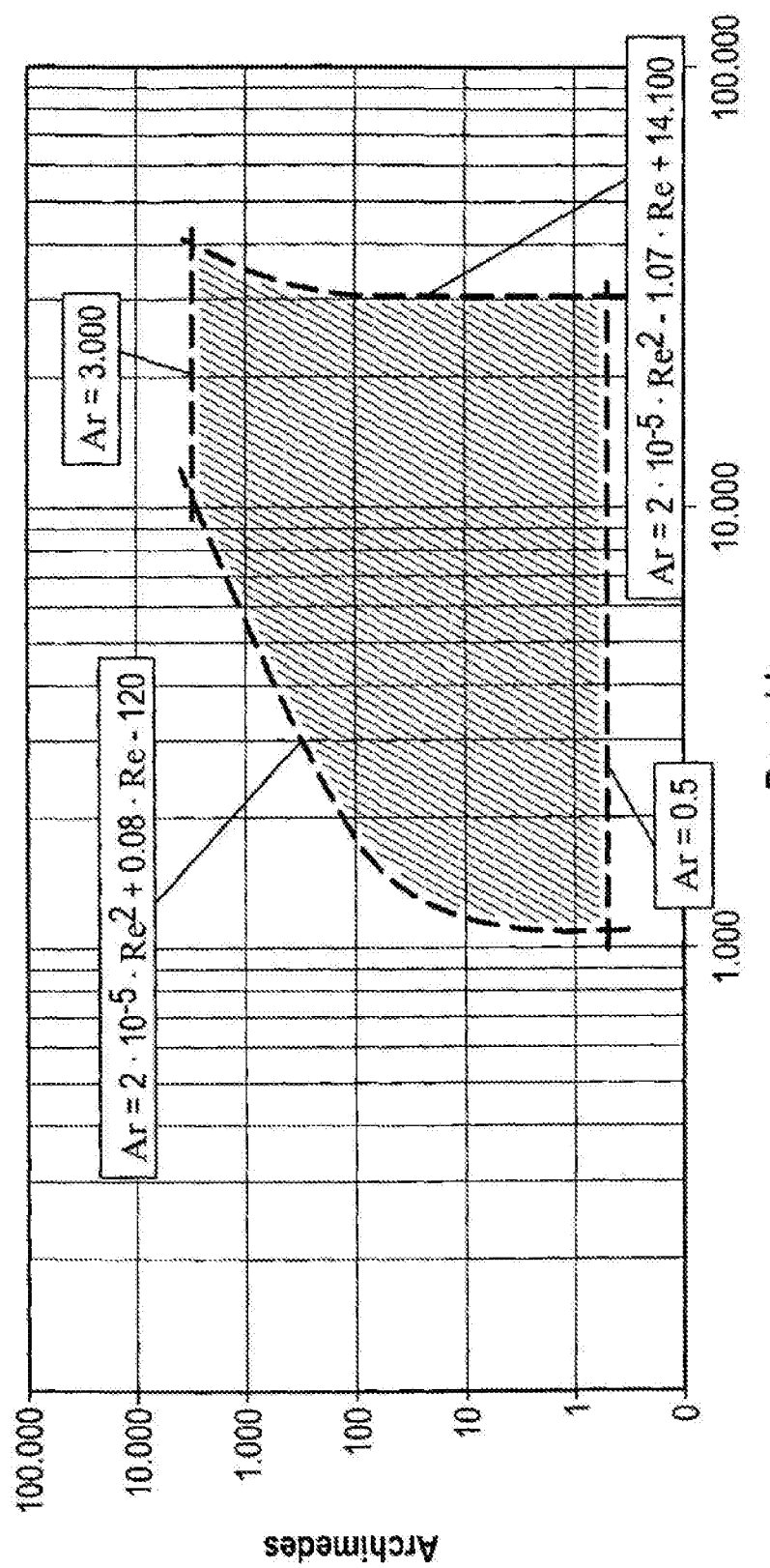
FIG. 1 depicts the Cartesian coordinate system in which Ar is plotted against Re.

The relationship between the internals geometry, expressed by the hydraulic plant diameter of the fluidized bed reactor, and the two operating parameters: superficial gas velocity in the fluidized bed reactor, and particle Sauter diameter of the catalytic composition, can be depicted in a diagram according to FIG. 1 by means of the two dimensionless parameters Archimedes number and Reynolds number.

The Archimedes number determined using equation 3 describes the influence of the relevant particle Sauter diameter of the catalytic composition on the fluid dynamics in the fluidized bed reactors.

The Reynolds number determined using equation 4 represents the superficial gas velocity in the fluidized bed reactor and thus the amount of reaction gas and gives the relationship to the fluidized bed reactor internals by means of the hydraulic plant diameter in the fluidized bed reactor as a characteristic reference length. A constant Reynolds number can thus be interpreted that the gas flow rate and therefore the volume stream of reaction gas may be increased at constant, open reactor cross-section, if the hydraulic plant diameter decreases through more internals surface area.

Based on the experimentally identified relationships, a working range can be defined with the aid of these two dimensionless parameters, Archimedes number and Reynolds number, in which the organochlorosilanes can be produced effectively and productively.

This range is characterized and limited on the one hand by Archimedes numbers between 0.5 and 3000 and on the other hand by Reynolds numbers whose lower limit is defined by equation 1 or whose upper limit is defined by equation 2.

This working range can be depicted in a Cartesian coordinate system in which Ar is plotted against Re. For this purpose, equations 1 and 2 and upper limits and lower limits of Ar form curves which demarcate a surface. The points on the surface form the working range in which the respective combinations of internals geometries, characterized by the hydraulic plant diameter of the fluidized bed reactor, superficial gas velocity in the fluidized bed reactor and the corresponding particle Sauter diameter of the catalytic composition, in which organochlorosilanes may be produced effectively and economically.

For the characterization of the particle sizes, the Sauter diameter is used, i.e. the average, particle diameter of equal volume to a particle in question.

Dimensionless Parameters:

The dimensionless Archimedes number may be interpreted as a ratio between buoyant force and friction force and serves to characterize the behaviour of different particles in fluidized layers. In this case, g corresponds to the acceleration due to gravity [m/s$^2$], $d_{32}$ to the particle Sauter diameter [m], $\rho_P$ to the particle solid density [kg/m$^3$], $\rho_F$ to the fluid density [kg/m$^3$] and $v_F$ to the kinematic viscosity of the fluid [m$^2$/s].

$$Ar = g \cdot \frac{d_{32}{}^3}{v_{F2}} \cdot \frac{\rho_P - \rho_F}{\rho_F} \qquad \text{Equation 3}$$

Using the dimensionless Reynolds number, the flow state of a fluid can be described. The Reynolds number may be interpreted as inertial force with respect to viscous force. As characteristic length, which is required for the definition of the Reynolds number, the hydraulic reactor or plant diameter is used and thus the reference to the influence of the reactor internals is produced. In this case, $u_L$ corresponds to the superficial gas velocity in the fluidized bed reactor [m/s], $d_{hyd}$ to the hydraulic reactor or plant diameter (equation 5) [m] and $v_F$ to the kinematic viscosity of the fluid [m$^2$/s].

$$Re = \frac{u_L \cdot d_{hyd}}{v_{Fluid}} \qquad \text{Equation 4}$$

Figure 3:
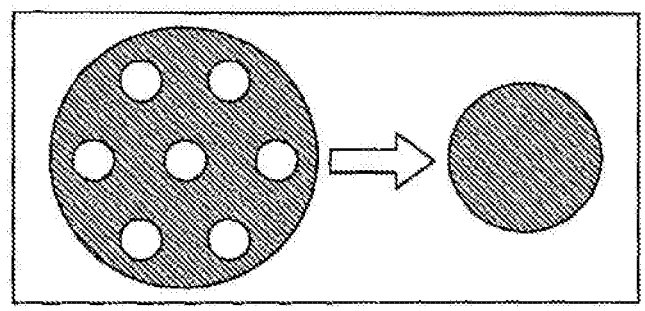
FIG. 3 illustrates two means of changing the hydraulic diameter of a reactor.

The hydraulic plant diameter in the fluidized bed reactor [m] is an engineering term, with which fluid mechanical friction and surface area effects of internals, channels, or different geometries can be described, in which these are a result of an equivalent tube diameter (see FIG. 3). The hydraulic diameter is calculated according to equation 5, where $A_{q,free}$ corresponds to the free cross-sectional flow [m²] and $U_{ges,wet}$ to the wet circumference in each case of all internals in the fluidized bed reactor [m].

$$d_{hyd} = \frac{4 * A_{q,free}}{U_{ges,wet}} \quad \text{Equation 5}$$

The invention also relates to a method for selecting reaction parameters for producing organochlorosilanes in a fluidized bed reaction by reacting organic compound having chlorine bound to carbon with a catalytic composition comprising silicon, copper catalysts and promoters in which the fluidized bed reaction is carried out in a fluidized bed reactor, wherein
the hydraulic diameter of the fluidized bed reactor $d_{hyd}$,
the superficial gas velocity in the fluidized bed reactor $u_L$ and
the particle Sauter diameter of the catalytic composition $d_{32}$ are selected as described above.

The hydraulic diameter of the fluidized bed reactor $d_{hyd}$ is preferably 0.1 m to 1.5 m, more preferably 0.15 m to 1.3 m, and especially 0.2 m to 1.1 m.

The superficial gas velocity in the fluidized bed reactor $u_L$ is preferably 0.02 m/s to 0.4 m/s, more preferably 0.05 m/s to 0.36 m/s, and especially 0.08 m/s to 0.32 m/s.

The particle Sauter diameter of the catalytic composition $d_{32}$ is preferably 5 µm to 300 µm, more preferably 10 µm to 280 µm, and especially 15 µm to 250 µm.

The catalytic composition is a mixture of solid particles comprising silicon, copper catalysts and promoters.

The silicon used in the process preferably comprises at most 5% by weight, more preferably at most 2% by weight, and especially at most 1% by weight of other elements as impurities. The impurities which make up at least 0.01% by weight, are elements preferably selected from Fe, Al, Ca, Ni, Mn, Cu, Zn, Sn, C, V, Ti, Cr, B, P, and O.

The copper for the catalyst may be selected from metallic copper, copper alloys or copper compounds. The copper compounds are selected preferably from copper oxides and copper chlorides, in particular CuO, $Cu_2O$ and CuCl, and a copper-phosphorus compound (CuP alloy). Copper oxide can be, for example, copper in the form of copper oxide mixtures and in the form of copper(II) oxide. Copper chloride may be used in the form of CuCl or in the form of $CuCl_2$, wherein appropriate mixtures are also possible. In a preferred embodiment, the copper is used as CuCl.

Based on 100 parts by weight silicon, preferably at least 0.1 parts by weight, particularly preferably at least 1 part by weight copper catalyst and preferably at most 10 parts by weight, especially at most 8 parts by weight copper catalyst are used, based in each case on metallic copper.

The catalytic composition preferably comprises one or more zinc promoters preferably selected from zinc and zinc chloride. Based on 100 parts by weight silicon, preferably at least 0.01 parts by weight zinc promoter, more preferably at least 0.05 parts by weight zinc promoter and preferably at most 1 part by weight, especially at most 0.5 parts by weight zinc promoter are used, based in each case on metallic zinc.

The catalytic composition preferably comprises one or more tin promoters preferably selected from tin and tin chloride. Based on 100 parts by weight silicon, preferably at least 0.001 parts by weight tin promoter, most preferably at least 0.002 parts by weight tin promoter and preferably at most 0.2 parts by weight, especially at most 0.1 parts by weight tin promoter are used, based in each case on metallic tin.

The catalytic composition preferably comprises a combination of zinc promoters and tin promoters and in particular additionally phosphorus promoters.

In addition to the zinc and/or tin promoters, further promoters may also be used which are preferably selected from the elements phosphorus, cesium, barium, manganese, iron and antimony, and compounds thereof.

The P promoter is preferably selected from CuP alloys.

The pressure in the fluidized bed reactor is preferably at least 1 bar, especially at least 1.5 bar and preferably at most 5 bar, especially at most 3 bar, specified in each case as absolute pressure.

The organic compound having chlorine bound to carbon is preferably a chloro-C1-C6-alkane, especially chloromethane. The organochlorosilanes produced are preferably $C_1$-$C_6$-alkylchlorosilanes, especially methylchlorosilanes. The methylchlorosilanes produced are preferably selected from dimethyldichlorosilane, methyltrichlorosilane, trimethylchlorosilane, dimethylchlorosilane and methyldichlorosilane. Particular preference is given to dimethyldichlorosilane.

The hydraulic diameter of the fluidized bed reactor $d_{hyd}$, the superficial gas velocity in the fluidized bed reactor $u_L$ and the particle Sauter diameter of the catalytic composition $d_{32}$ are preferably selected such that, in the fluidized bed reaction, high productivity and/or selectivity for the organochlorosilanes produced is achieved. These are preferably selected such that high productivity and/or selectivity for dimethyldichlorosilane is achieved.

In addition to chloromethane, the reaction gas may comprise a carrier gas selected from $N_2$ and noble gases such as Ar. The reaction gas preferably comprises at least 50% by volume, more preferably at least 70% by volume, and especially at least 90% by volume of chloromethane.

All symbols above of the formulae above are each defined independently of one another.

In the following examples, unless stated otherwise in each case, all amounts and percentages refer to weight, all pressures 0.10 MPa (abs.) and all temperatures 20° C.

Examples

The relationship described above between internals, particle sizes and particle discharge were verified initially without chemical reaction in a pilot fluidized bed. This showed that there is an exponential relationship between the hydraulic reactor or plant diameter and the particle discharge. This relationship was measured and confirmed for different internals and particle size distributions.

General Examples

Increasing the fluidized bed reactor productivity at constant catalytic composition particle size in existing reactors: by decreasing the hydraulic plant diameter (by additional sheet-like internals or heat exchange tubes), the particle discharge from the reactor is initially reduced. The additional latitude in the particle discharge may be used by increasing the gas flow rate, whereupon the productivity in the range identified increases.

Increasing the reactor productivity by reducing the catalytic composition particle sizes in existing reactors: a lower particle size leads to a higher particle discharge from the reactor. This can be reduced in turn by reducing the hydraulic plant diameter so that a more productive particle size with greater surface area may be used or to reduce the silicon losses.

Design of novel fluidized bed reactors: taking into account the aforementioned expertise, novel synthesis reactors may be modified optimally, with respect to the dimensions, the internals and the operational settings, to an (optimal) catalytic composition particle size. These combinations correspond to the area indicated in FIG. 1.

Figure 4:
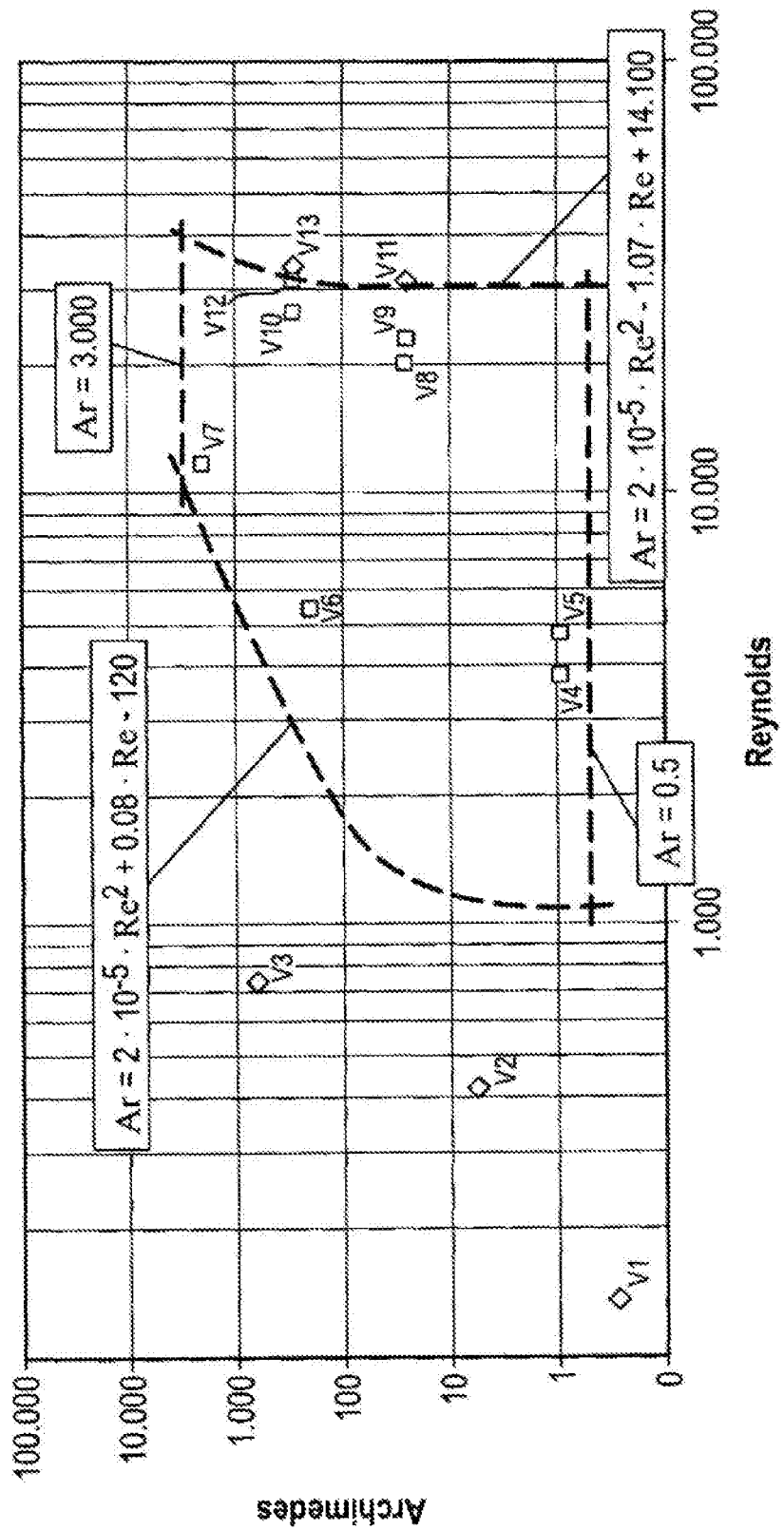
FIG. 4 shows boundary conditions with respect to low Archimedes numbers.

Experiments: in order to be able to apply the expertise and relationships obtained to the productivity of the MCS synthesis and to define the aforementioned limits of the influencing factors, detailed investigations of various continuously operating fluidized bed reactors and reactor sizes were carried out. By varying the hydraulic plant diameter $d_{hyd}$ between 0.1 m and 1.0 m, the superficial gas velocity $u_L$ between 0.03 m/s and 0.3 m/s, and the particle Sauter diameter between 15 μm and 250 μm, the experimental results shown in Table 1, with the corresponding Reynolds and Archimedes numbers, were achieved. The measure of the productivity with respect to the limitation of the combinations of Reynolds and Archimedes numbers selected was based on the amount of dichlorodimethylsilane produced per hour [kg/h], relative to the catalytic composition reactor content [kg], i.e. [kg/(kg*h)], which exceeds 0.15 kg/(kg*h). The results of these investigations, summarized in FIG. 4, show the graphical classification of the measurement results. Shown are firstly the measurements within the defined range (squares, V4-V10 & V12), whose productivity is greater than 0.15 kg/(kg*h), against which the measurement results depicted as diamonds (V1-3, V11 & V13) have lower productivities, i.e. less than 0.15 kg/(kg*h).

TABLE 1

|  | Reynolds | Archimedes | Productivity [kg/(kg*h)] |
|---|---|---|---|
| V1 | 136 | 0.3 | 0.025 |
| V2 | 420 | 5.5 | 0.027 |
| V3 | 738 | 628.0 | 0.006 |
| V4 | 3.758 | 0.9 | 0.310 |
| V5 | 4.698 | 0.9 | 0.374 |
| V6 | 5.399 | 198.9 | 0.217 |
| V7 | 11.609 | 1966.1 | 0.226 |
| V8 | 19.928 | 25.2 | 0.282 |
| V9 | 22.628 | 24.0 | 0.278 |
| V10 | 26.201 | 278.9 | 0.189 |
| V11 | 30.964 | 24.0 | 0.110 |
| V12 | 31.073 | 278.9 | 0.165 |
| V13 | 33.346 | 278.9 | 0.099 |

The range limits for low Reynolds numbers (equation 1) is characterized in that combinations of low gas flow rate and/or very low hydraulic reactor diameter lead to decreasing production amounts. This effect increases with increasing particle size (Archimedes number), since for coarser particles comparatively higher gas flow rates are required for the fluidization, which can be seen from the shape of the curve (Equation 1, FIG. 1). The range limits for high Reynolds numbers (Equation 2) is characterized by very high gas flow rates such that, for example, the particle discharge can no longer be compensated for by adjusting the hydraulic reactor diameter. It can also be seen here that for coarser particles (higher Archimedes number), a comparatively broader range can be specified since, for example, the particle discharge negatively effects the productivity only in combinations of relatively high gas flow rate and hydraulic plant diameter. The boundary of the defined range (FIG. 4) with respect to the Archimedes numbers <0.5, i.e. for very fine particles, results on the one hand in the fact that the particle discharge can no longer be adequately compensated for by reducing the hydraulic plant diameter, which results in an uneconomic plant operation, and on the other hand the fact that in this range the limits of an effective fluidization capacity of the catalytic composition are reached, such that the productivity decreases due to decreased gas/solid contact. At the upper end of the range of Archimedes numbers (>3000) are coarser particles which firstly require comparatively high fluidization rates and secondly depart the economic range of high productivity owing to lower specific particle surface area.

The invention claimed is:

1. A process for producing organochlorosilanes in a fluidized bed reaction comprising reacting a reaction gas comprising organic compound having chlorine bound to carbon, with catalytic composition comprising silicon, copper catalysts and promoters, in a fluidized bed reactor, the improvement comprising selecting the hydraulic diameter of the fluidized bed reactor dhyd, the superficial gas velocity in the fluidized bed reactor uL and the particle Sauter diameter of the catalytic composition d32, such that, in a Cartesian coordination system, in which Ar is plotted against Re, points on the surface are formed wherein the surface is limited by equations 1 and 2

$$Ar = 2 \cdot 10^{-5} \cdot Re^2 + 0.08 * Re - 120 \qquad \text{Equation 1:}$$

$$Ar = 2 \cdot 10^{-5} \cdot Re^2 - 1.07 * Re + 14100 \qquad \text{Equation 2:}$$

wherein the lower limit Ar=0.5 and
the upper limit Ar=3000,
where Ar is the dimensionless Archimedes number, which is determined by equation 3

$$Ar = g \cdot \frac{d_{32}^3}{v_F^2} \cdot \frac{\rho_P - \rho_F}{\rho_F} \qquad \text{Equation 3}$$

where
g is the acceleration due to gravity [m/s$^2$],
d32 is the particle Sauter diameter [m],
ρP is the particle solid density [kg/m$^3$],
ρF is the fluid density [kg/m$^3$],
vF is the kinematic viscosity of the fluid [m$^2$/s],
where Re is the dimensionless Reynolds number, which is determined by equation 4

$$Re = \frac{u_L \cdot d_{hyd}}{v_F} \qquad \text{Equation 4}$$

where
uL is the superficial gas velocity in the fluidized bed reactor [m/s],
dhyd is the hydraulic plant diameter [m] in the fluidized bed reactor, which is determined by equation 5

$$d_{hyd} = \frac{4 * A_{q,free}}{U_{ges,wet}} \qquad \text{Equation 5}$$

where
Aq,free is the free cross-sectional flow [m$^2$] in the fluidized bed reactor and U$_{ges,wet}$ corresponds to the wet circumference [m] in each case of all internals in the fluidized bed reactor,
and wherein the hydraulic diameter of the fluidized bed reactor d$_{hyd}$ is from 0.2 m to 1.5 m.

2. A method for selecting reaction parameters for producing organochlorosilanes in a fluidized bed reaction by reacting organic compound(s) having chlorine bound to carbon with a catalytic composition comprising silicon, copper catalysts and promoters, in which the fluidized bed reaction is carried out in a fluidized bed reactor, comprising selecting the hydraulic diameter of the fluidized bed reactor d$_{hyd}$, the superficial gas velocity in the fluidized bed reactor u$_L$ and the particle Sauter diameter of the catalytic composition d$_{32}$, as in claim 1.

3. The process of claim 1, wherein the superficial gas velocity in the fluidized bed reactor u$_L$ is 0.02 m/s to 0.4 m/s.

4. The process of claim 1, wherein the particle Sauter diameter of the catalytic composition d$_{32}$ is 5 μm to 300 μm.

5. The process of claim 1, wherein the silicon particle size is 0.5 to 650 micrometers.

6. The process of claim 1, wherein the reaction gas comprises at least 50% by volume of organic compound(s) having chlorine bound to carbon.

7. The process of claim 1, wherein the organic compound having chlorine bound to carbon is chloromethane and the organochlorosilanes produced are methylchlorosilanes.

* * * * *